United States Patent [19]

Bhatia

[11] Patent Number: 5,266,706
[45] Date of Patent: * Nov. 30, 1993

[54] SOLVENT SCRUBBING RECOVERY OF LACTIDE AND OTHER DIMERIC CYCLIC ESTERS

[75] Inventor: Kamlesh K. Bhatia, Newark, Del.

[73] Assignee: E. I. Du Pont de Nemours & Company, Wilmington, Del.

[*] Notice: The portion of the term of this patent subsequent to May 26, 2007 has been disclaimed.

[21] Appl. No.: 828,547

[22] Filed: Jan. 28, 1992

Related U.S. Application Data

[62] Division of Ser. No. 602,346, Oct. 23, 1990, Pat. No. 5,117,008.

[51] Int. Cl.$^5$ .................................... C07D 319/00
[52] U.S. Cl. ......................................... 549/274
[58] Field of Search ................................ 549/274

[56] References Cited

U.S. PATENT DOCUMENTS

| | | | |
|---|---|---|---|
| 1,095,205 | 5/1914 | Gruter et al. | 549/274 |
| 2,668,162 | 2/1954 | Lowe | 549/274 |
| 4,727,163 | 2/1988 | Bellis | 549/274 |
| 4,835,293 | 5/1989 | Bhatia | 549/274 |
| 5,117,008 | 5/1992 | Bhatia et al. | 549/274 |

FOREIGN PATENT DOCUMENTS 3632103 9/1986 Fed. Rep. of Germany .
3708915 3/1987 Fed. Rep. of Germany .

Primary Examiner—C. Warren Ivy
Assistant Examiner—A. Owens
Attorney, Agent, or Firm—Don O. Winslow

[57] ABSTRACT

An improved process for the recovery of lactide or other dimeric cyclic ester from a gas stream containing the cyclic ester and such hydroxylic impurities as water and open-chain hydroxycarboxylic acids, by scrubbing the gas stream with a water immiscible solvent, such as, a non-polar hydrocarbon, a cycloaliphatic hydrocarbon or a halogenated hydrocarbon solvent, at a temperature at which the cyclic ester and the open-chain hydroxycarboxylic acids are scrubbed from the gas stream and any water present in the gas stream is carried away. The crude cyclic ester-acid composition is separated from the solvent and purified by extracting the acid impurities therefrom. The acid impurities are recovered and recycled.

11 Claims, No Drawings

SOLVENT SCRUBBING RECOVERY OF LACTIDE AND OTHER DIMERIC CYCLIC ESTERS

CROSS-REFERENCE TO RELATED APPLICATION

This is a continuation-in-part of application Ser. No. 07/602,346, filed Oct. 23, 1990 now U.S. Pat. No. 5,117,008.

BACKGROUND OF THE INVENTION

1. Field of the Invention

This invention relates to a solvent scrubbing process for the recovery of dimeric cyclic esters from impure reaction product streams. In particular it relates to such recovery of the cyclic esters from gas product streams also containing water and acids as impurities by scrubbing with a non-polar water immiscible solvent, more particularly counter-currently, at a temperature at which the cyclic ester and the acid impurities are precipitated by the solvent and any water present in the gas stream is vaporized from the solvent.

2. Description of the Related Art

The preparation of dimeric cyclic esters of alpha-hydroxycarboxylic acids is an old and much studied process. The preparation is normally conducted in two stages involving first preparing an oligomer of the hydroxycarboxylic acid; i.e., a relatively short-chain condensation polymer thereof, then heating the oligomer to depolymerize it to the desired cyclic ester, see for example: Gruter et al., U.S. Pat. No. 1,095,205 (1914); Lowe, U.S. Pat. No. 2,668,162 (1954); Bhatia, U.S. Pat. No. 4,835,293 (1989); Bellis U.S. Pat. No. 4,727,163 (1988); and Muller, Ger. Pat. Applications 3632103 and 3708915 (1988). In the preparation of the oligomers from the corresponding alpha-hydroxycarboxylic acids the water of condensation is difficult to completely remove from the polymer. Water is also formed in the depolymerization step so that the cyclic ester depolymerization product generally contains water as an impurity. The cyclic ester may also contain one or more open-chain hydroxycarboxylic acids as impurities. All such hydroxylic impurities are undesirable as they act as chain-stoppers in the subsequent polymerization of the cyclic ester to the high molecular weight products required for biomedical and other uses. It is therefore desired to keep the water and open-chain hydroxycarboxylic acid content of the dimeric cyclic ester as low as practicable.

Bhatia U.S. Pat. No. 4,835,293 discloses an improved depolymerization and product recovery process for the production of dimeric cyclic esters such as lactide wherein a stream of an inert gas is employed to strip the cyclic ester from the reaction zone along with any water and/or volatile hydroxycarboxylic acid also formed therein. The resulting gaseous product stream is scrubbed with a polar organic solvent to recover the cyclic ester. The solvents include alcohols, ethers, esters and ketones, with use of isopropyl alcohol exemplifying the recovery of glycolide from its impurities. Isopropyl alcohol as scrubbing solvent solubilizes the hydroxycarboxylic acids and any water present, thereby enabling the recovery of glycolide directly from the scrubbing medium as a substantially insoluble filterable crystalline solid.

Use of an alcohol, however, as the scrubbing solvent for the recovery of glycolide, lactide or other such cyclic ester from a vapor product stream is not entirely satisfactory. The alcohol, as well as the solubilized water and acids, can all react with the cyclic ester in the alcoholic solution to form additional open-chain products, which not only constitute a yield loss but further tend to increase the solubility of the cyclic ester in the scrubbing solution, further aggravating the yield loss problem.

It will be appreciated that although the proportions of water and of by-product (for example, lactic acid) in a cyclic ester such as lactide may be relatively small, their potentially detrimental effect on product yield can be large. Water, for example, is capable of reacting with eight times its own weight of lactide and convert it to by-product open-change dimer.

Thus, a need exists for a means that provides for the substantially complete recovery of a cyclic ester such as lactide from a vapor stream that also contains open-chain acids as well as water. A need also exists for such a process that also provides for the substantially complete recovery of the acid values as well as the cyclic ester.

SUMMARY OF THE INVENTION

The present invention provides, in a gas-assisted process for depolymerizing an oligomeric poly(hydroxycarboxylic acid) to a dimeric cyclic ester, which involves, (i) heating the oligomer in a reaction zone under depolymerizing conditions effective to generate the cyclic ester, (ii) passing a stream of an inert gas through the oligomeric material at a rate and in an amount sufficient to sweep the cyclic ester and any water present from the reaction zone and to form a gas stream containing the cyclic ester, open-chain hydroxycarboxylic acid impurities and any water entrained therewith and (iii) scrubbing the gas stream with a solvent in a scubber to remove the cyclic ester therefrom, wherein the improvement comprises:

(a) employing as the scrubbing solvent a water-immiscible aliphatic or cycloaliphatic hydrocarbon or halogenated hydrocarbon;

(b) conducting the scrubbing step at a temperature at which most of the water is carried away with the gas stream and substantially all of the product is retained in the scrubber along with the solvent; and (c) separating the product from the solvent.

Preferably the temperature is such that the cyclic ester and the acid impurities comprise a solid phase.

In one embodiment of the invention the recovered product, comprising the cyclic ester, its acid impurities and any occluded water not carried off in the gas stream, is further treated to separate the cyclic ester from the impurities. Such treatments may include washing the recovered product composition with a polar solvent that is a good solvent for the impurities but a relatively poor solvent for the cyclic ester, and/or recrystallizing the cyclic ester from a suitable inert solvent having greater solvency for the impurities than the cyclic ester. The acid impurities, consisting largely of monomeric alpha-hydroxycarboxylic acid and/or its open chain dimer, can be recovered from these solvents (i.e., the washing and recrystallizing solvents) by conventional techniques and, if desired, recycled to a process for the preparation of additional oligomer to be converted to cyclic ester.

In other, more specific embodiments, the oligomer is a relatively low molecular weight polymer of glycolic and/or lactic acid, including aqueous lactic acid such as the 80–90% acid available commercially, and the scrubbing solvent boils in the range of from about 45° to about 200° C.

Overall, the invention process provides for improved recovery yields of the desired dimeric cyclic esters as well as recovery of recyclable acid impurities vaporized therewith, thereby affording still higher overall production yields.

DETAILED DESCRIPTION OF THE INVENTION

The invention is applicable to the treatment of impure dimeric cyclic esters containing hydroxylic impurities such as water and open-chain hydroxycarboxylic acids. It is particularly applicable to the treatment of a vapor stream containing the impure cyclic ester, more particularly where the impure cyclic ester is a lactide composition. The invention process broadly comprises contacting a gas stream containing a dimeric cyclic ester as defined and water and/or acid impurities as defined with a non-polar solvent as defined in an amount and at a temperature at which the cyclic ester and the acid impurities precipitate from the gas stream, preferably as a solid composition, and the water is volatilized therefrom, thereby effecting separation of the cyclic ester and the acids from the water impurity. The solvent is chosen such that the cyclic ester and the acids are substantially insoluble therein. The cyclic ester and the acid impurities are then separated from the solvent by any means known to the art, such as filtration or centrifugation.

The cyclic ester can be separated from the acid impurities employing methods known in the art, for example, washing with or recrystallizing from a solvent in which the acid impurities are more soluble than the cyclic ester. Such solvents include water, alcohols, for example, isopropyl alcohol and amyl alcohols, ketones such as acetone, methyl ethyl ketone, and esters such as ethyl acetate.

L- (or D-) lactide generated from commercial L- (or D-) lactic acid, which generally contains some D- (or L-) isomer, normally contains some meso-lactide. When the product is D- or L-lactide containing some meso-lactide, it is preferable to remove the acid impurities by extraction with water. The acids can then be recovered by concentrating the water solution and recycled along with fresh acid feed to increase the overall process yield without building up meso-lactide in the system. The acid-free D- and L-lactide thus obtained contains some meso-lactide. If it is desired that the product contain no meso-lactide, the meso isomer can be removed by washing the product with or recrystallizing it from a solvent in which the meso is more soluble than the D or L isomer. Such solvents include alcohols, ketones and esters mentioned above as well as aromatic solvents such as toluene.

The gas stream containing the impure dimeric cyclic ester may be that generated in a gas-assisted depolymerization process as described by Bhatia in U.S. Pat. No. 4,835,293, which disclosure is incorporated herein by reference. In general such gas-assisted depolymerization process comprises heating an oligomer of an alpha-hydroxycarboxylic acid, e.g. glycolic or lactic acid, to a temperature at which the oligomer is molten and depolymerizable to the corresponding dimeric cyclic ester, usually and preferably in the presence of a depolymerization catalyst, while passing an inert gas through the molten oligomer in an amount and at a rate sufficient to entrain the cyclic ester from the reaction mass, preferably as fast as it is formed. The resulting gas product stream normally also contains water and other volatile materials such as open-chain carboxylic acids.

In accordance with the present invention, a gas stream generated in the above referenced depolymerization process is scrubbed with a non-polar organic solvent as defined to remove the cyclic ester and hydroxycarboxylic acids from the gas stream and separate them from any water present in the stream. The scrubbing solvent may be any substance that is liquid below about 40° C., non-polar and water-immiscible, hence a non-solvent for water, the acids and the cyclic ester at the operating temperature, and is stable and inert to the product stream components under the scrubbing conditions.

The boiling point of the solvent is not critical but it should be high enough to prevent excessive loss of it in the exiting gas stream. Thus solvents having boiling points of about 45° C. may be used, with those boiling at at least about 75° C. preferred, and those boiling between about 90° and 200° C. more preferred.

By "non-solvent" for water at the operating temperature is meant that water will flash off the scrubbing solvent and pass out of the scrubbing zone as a vapor stream. By "non-solvent" for the alpha-hydroxycarboxylic acid(s) is meant that such component(s) will substantially completely separate out from the solvent along with the cyclic ester to form a separate phase.

Suitable solvents are aliphatic and cyclo-aliphatic hydrocarbons and halogenated derivatives thereof. Representative are 2,2-dimethylbutane, n-hexane, 2-methylpentane, n-heptane, n-decane, 1-decene, cyclopentane, cyclohexane, dimethylcyclohexane (including the individual and the mixed 1,2-1,3- and 1,4-isomers), $CCl_2FCCl_2F$, $CCl_2FCClF_2$, $CF_3CCl_3$ and mixtures of any two or more thereof.

The operating temperature, that is, the temperature at which the scrubbing medium is maintained during the cyclic ester stripping operation, can vary widely depending on the particular cyclic ester and solvent involved. It is preferred to keep the temperature of the liquid scrubbing medium low so as to minimize loss of solvent, possible reaction of acid impurities with the cyclic ester, and loss of cyclic ester to the gas stream. But it should be sufficiently high to drive the water overhead.

Thus the temperature of the scrubbing medium will be generally between the ambient temperature and about 130° C., preferably between ambient temperature and 60° C. The lower temperature limit is designed to allow for cooling economically. Use of sub-ambient temperatures including 0° C., however is contemplated and falls within the scope of this invention.

The pressure throughout the scrubbing step may vary from sub-atmospheric to atmospheric and super-atmospheric. Conveniently and preferably it will be about atmospheric pressure.

The invention process is applicable to the recovery of dimeric cyclic esters having the formula

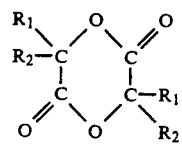

where each R group is independently H or a $C_1$ to $C_6$ hydrocarbyl. Preferably each R group is H or a $C_1$ to $C_3$ alkyl group, more preferably H or methyl. Typical dimeric cyclic esters include glycolide (R1=R2=H), lactide (R1=H, R2=CH3), tetramethylglycolide, sym-diethylglycolide, the dimeric cyclic ester of alpha-hydroxyvaleric acid and the like. Preferred are glycolide, lactide (including L-, D- and meso-lactide) and mixtures of glycolide with one or more of the isomeric lactides.

The steps of polymerizing the alpha-hydroxycarboxylic acid, $HOC(R_1R_2)CO_2H$, where $R_1$ and $R_2$ are as defined above, to an oligomer and of depolymerizing the oligomer to a cyclic ester are ordinarily and preferably conducted in the presence of a catalyst. The catalyst can be any of those known in the art for promoting condesation of the alpha-hydroxycarboxylic acid to oligomers and for promoting cyclic ester formation. The catalysts are generally metals or compounds of metals of groups IV, V and VIII of the Periodic Table. Preferred are metals of groups IV, notably Sn as the metal (powdered), oxide, halogenide or carboxylate, or V, notably Sb, usually as the oxide $Sb_2O_3$. Preferred herein are Sn(II) carboxylates, exemplified by Sn bis (2-ethylhexanoate), commonly referred to as stannous octoate.

The catalyst is employed in catalytically effective amounts, which can vary widely depending upon reaction conditions. The optimum catalytically effective amounts for any particular system can readily be determined through trial runs.

The gaseous agent for entraining/carrying/sweeping the cyclic ester and the impurities out of the reaction mixture and out of the depolymerization reactor may be any substance that is gaseous, stable and non-reactive at the operating temperatures and pressures and is inert to the starting material, reaction mass components and reaction products. It may be normally gaseous, such as nitrogen, argon, carbon monoxide or dioxide or low molecular weight hydrocarbon. It may be normally non-gaseous but gaseous at reaction temperature and pressure. Preferred is nitrogen for its inertness and ready availability. Preferably the inert gas will be preheated to the operating temperature and will be injected below the surface of the reaction mass in the reaction zone; for example, below the agitator of a stirred tank reactor or at the bottom of a vertically disposed reactor.

The flow rate of the gas should be sufficiently high so as not to limit the cyclic ester stripping rate. If the flow rate is too low, the conversion to cyclic ester may be adversely affected and its production rate limited since the gas functions importantly to carry it as vapor out of the reactor.

The depolymerizer reactor design is not critical provided it has means for introducing an oligomeric feed stream, means for introducing a gaseous cyclic ester stripping agent into the reaction zone such that it directly and intimately contacts the oligomeric composition so as to give high gas-liquid interfacial contact and has means for removing a gaseous stream containing cyclic ester. Thus the reactor may be a stirred tank equipped with gas-sparging means, preferably one which admits the gas directly under the agitator. The reactor may also be a packed or sieve-plate column, or it may be of any other design known in the art for effecting intimate gas-liquid contact.

Preferably, the depolymerization step is conducted in a continuous manner with the oligomer fed to the reactor continuously at a controlled rate such that hold-up of polymeric material within the reactor is minimized. In this way degradation of oligomer to unwanted by-products can be minimized and conversion to cyclic ester maximized. Thus, treating a gas stream from such a continuous depolymerization process by the present invention method would yield a still higher quality cyclic ester product.

The following examples were conducted in an apparatus comprising a gas-assisted depolymerization unit in association with a counter current scrubbing unit. Unless otherwise specified, commercially available reagent grade materials were employed.

EXAMPLE 1

Lactic acid oligomer was prepared starting with 756.1 gms of 88% L-lactic acid (Aldrich Chem. Co.) equivalent to 532.2 gms of lactide and using 2.6 gms of stannous acetate (M&T Chemicals) as the catalyst. The acid was heated gradually to 187° C. to remove free water and water of condensation. To assist in removing the water and complete the oligomerization, a stream of $N_2$ at 0.15 SCFM (standard cubic feet per minute) was passed through the reaction mass for about 30 minutes until no more water was seen condensing out.

The oligomer was then cracked for 2 hours and 40 minutes while maintaining its temperature between 215°-227° C. and removing reaction products in a stream of $N_2$ fed at 0.3 SCFM. The $N_2$ stream containing the reaction products was scrubbed with 1-decene. The decene temperature ranged between 103°-133° C. but was mostly between 103° and 120° C. When reaction product ceased coming over, the cracking was stopped and the decene product mix allowed to cool. Crude lactide solidified upon cooling and was filtered to give 452.5 gms of filter cake. It was slurried with isopropyl alcohol (IPA) to dissolve away the acid impurities and filtered again. The new filter cake was washed with fresh IPA, then with toluene. The resulting "wet" filter cake weighed 320 gms, which upon drying amounted to 304.6 gms of white lactide product. This was about 1.5 times the approximately 200 gms obtained in similar runs using IPA as the scrubbing solvent. The uncracked oligomer left in the reactor weighed 36.6 gms. Yield, based on the amount of oligomer cracked, was 452.5/(532.2−36.6)=91.3% to the crude product and 304.6/(532.2−36.6)=61.4% to the lactide product remaining after washing away the acid impurities.

The lactic acid contained in the above washings could be recovered by evaporating off the wash solvents and recycled to the oligomerization step to increase the overall process yield.

EXAMPLE 2

Lactic acid oligomer was prepared as in Example 1 starting with 753.2 gms of 88% L-lactic acid (equivalent to 530.3 gms of lactide) containing 2.78 gms of stannous octoate.

It was cracked for 1.5 hours at 206°-214° C. as in Example 1, but with n-decane at 124°-130° C. used for scrubbing. 180.2 gms of filter cake was recovered.

The unconverted oligomer remaining was reheated the next day and cracked for 3 more hours under the above conditions, except that towards the end the temperature was raised to 229° C. and the $N_2$ flow rate increased to 0.4 SCFM. At the end of this cracking period, 57.3 gms remained unconverted. 195.2 gms of product was filtered out of the decane for a total of 180.2+195.2=375.4 gms of crude product. 90 gms of the product was washed with IPA, then recrystallized from IPA and dried to yield 69.5 gms of white lactide crystals. Its purity determined by Differential Scanning Calorimetry (DSC) was 99%. Its melting point was 96.1° C. and its optical rotation −285 degrees.

From the above results, the yield based on the amount of oligomer cracked was 375.4/(530.3−57.3)=79.4% to the crude lactide product and (69.5/90)×79.4%=61.3% to the refined recrystallized product.

EXAMPLE 3

This was run using n-heptane as the scrubbing solvent.

The procedure employed was the same as in Examples 1 and 2 except that 1. 765.3 gms of 88% L-lactic acid and 2.41 gms of stannous octoate catalyst were used.
2. Cracking was done for 3¼ hours at 203°-210° C. The N2 flow rate during the first hour was 0.05 SCFM but was then raised to 0.3 SCFM.
3. The scrubber was cooled to around 50° C., well below the melting point of product which collected as solid. 290 gms of oligomer remained uncracked as heel.
4. The free water and the water of condensation collected during oligomerization was evaporated and found to contain 22.6 gms of lactic acid.
5. The crude product filtered form heptane weighed 195.3 gms. It was then washed with IPA and finally recrystallized from IPA.

Yield to the crude product (195.3 gms), based on the amount of oligomer cracked and correcting for the 22.6 gms lactic acid recovered during oligomerization, was 83.9%.

The crude product was refined by washing it and recrystallizing it from IPA; the refining yield was 71.5%.

The refined product; i.e., water- and IPA-washed and recrystallized, was 99.2% pure L-lactide by DSC and melted at 97.7° C. Its optical rotation was −296 degrees. High pressure liquid chromatography on a chiral column showed no meso- or D-isomer present in the refined product.

Thus, the overall yield from 88% lactic acid to the refined product was 0.839×0.715×100 or 60%.

Having thus described and exemplified the invention with a certain degree of particularity, it should be appreciated that the following claims are not to be so limited but are to be afforded a scope commensurate with the wording of each element of the claim and equivalents thereof.

What is claimed:

1. In a gas-assisted process for depolymerizing an oligomeric poly(hydroxycarboxylic acid) to a dimeric cyclic ester, which involves, (i) heating the oligomer in a reaction zone under depolymerizing conditions effective to generate the cyclic ester, (ii) passing a stream of an inert gas through the oligomeric material at a rate and in an amount sufficient to sweep the cyclic ester and any water present from the reaction zone and to form a gas stream containing the cyclic ester, open-chain hydroxycarboxylic acid impurities and any water entrained therewith and (iii) scrubbing the gas stream with a solvent in a scrubber to remove the cyclic ester therefrom, wherein the improvement comprises:
   (a) employing as the scrubbing solvent a water-immiscible aliphatic or cycloaliphatic hydrocarbon which is 2,2-dimethylbutane, n-hexane, 2-methylpentane, n-heptane, n-decane, 1-decene, cyclopentane, cyclohexane, 1,2-dimethylcyclohexane, 1,3-dimethylcyclohexane, 1,4-dimethylcyclohexane or a mixture of any two or more thereof;
   (b) conducting the scrubbing step at a temperature at which most of the water is carried away with the gas stream and substantially all of the product is retained in the scrubber along with the solvent; and
   (c) separating the product from the solvent as a substantially solid phase.

2. The process of claim 1 wherein the product is collected in the solvent as a substantially insoluble solid phase and is separated from the solvent as a solid.

3. The process of claim 1 wherein the acid impurities are extracted from the product with a polar solvent in which the cyclic ester is only sparingly soluble.

4. The process of claim 3 wherein the polar solvent is water and the resulting aqueous stream containing the acid impurities is concentrated to recover the acid value which is recycled to a process for converting it to an oligomer thereof.

5. The process of claim 1 wherein the scrubbing solvent boils in the range of about 45° to about 200° C. and the scrubbing temperature is in the range of from about ambient temperature to about 130° C.

6. The process of claim 5 wherein the solvent boils at a temperature of at least about 75° C. and the scrubbing temperature is in the range of from about ambient to about 60° C.

7. The process of claim 1 wherein the oligomer is an oligomer of an alpha-hydroxycarboxylic acid, $HOC(R_1R_2)CO_2H$, and the dimeric cyclic ester has the formula $$\begin{array}{c} R_1 \quad\quad O \quad\quad O \\ \diagdown \quad \diagup \diagdown \quad \diagup\!\!\!\!\diagup \\ R_2\!-\!C \quad\quad C \\ | \quad\quad\quad | \\ C \quad\quad C\!-\!R_1 \\ \diagup\!\!\!\!\diagup \diagdown \quad \diagup \diagdown \\ O \quad\quad O \quad\quad R_2 \end{array}$$

wherein each R1 or R2 group in the hydroxy acid and the cyclic ester is independently H or a C1 to C6 hydrocarbyl radical.

8. The process of claim 7 wherein each R1 or R2 group is H or a C1 to C3 alkyl group.

9. The process of claim 8 wherein the alkyl groups when present are methyl groups.

10. The process of claim 9 wherein the hydroxy acid is glycolic or lactic acid and the cyclic ester is glycolide or lactide.

11. The process of claim 10 wherein the acid is L-lactic acid and the cyclic ester is L-lactide.

* * * * *